United States Patent
Sawa et al.

(10) Patent No.: US 8,087,282 B2
(45) Date of Patent: Jan. 3, 2012

(54) TEST MANAGEMENT METHOD FOR INDENTATION TESTER AND INDENTATION TESTER

(75) Inventors: Takeshi Sawa, Kawasaki (JP); Masaru Kawazoe, Kawasaki (JP); Kenji Okabe, Kawasaki (JP)

(73) Assignee: Mitutoyo Corporation, Kawasaki (JP)

( * ) Notice: Subject to any disclaimer, the term of this patent is extended or adjusted under 35 U.S.C. 154(b) by 437 days.

(21) Appl. No.: 12/222,267

(22) Filed: Aug. 6, 2008

(65) Prior Publication Data

US 2009/0044609 A1 Feb. 19, 2009

(30) Foreign Application Priority Data

Aug. 13, 2007 (JP) .................... 2007-210818

(51) Int. Cl.
*G01G 21/30* (2006.01)
*G01N 3/48* (2006.01)

(52) U.S. Cl. ............................. 73/1.89; 73/81

(58) Field of Classification Search .............. 73/81, 1.89, 73/78, 105
See application file for complete search history.

(56) References Cited

U.S. PATENT DOCUMENTS

| | | | | |
|---|---|---|---|---|
| 4,691,559 A | * | 9/1987 | Fischer | 73/81 |
| 4,848,141 A | * | 7/1989 | Oliver et al. | 73/81 |
| 6,146,013 A | * | 11/2000 | Huetter et al. | 374/46 |
| 2004/0011119 A1 | * | 1/2004 | Jardret et al. | 73/81 |

FOREIGN PATENT DOCUMENTS

| | | |
|---|---|---|
| JP | A-2002-181679 | 6/2002 |
| JP | A-2004-012178 | 1/2004 |
| WO | WO 2006069847 A1 * | 7/2006 |

OTHER PUBLICATIONS

Klyuev, V. P. Indenter Penetration Viscometry of Glasses for Small-Sized Samples under Conditions of Continuous Heating. Glass Physics and Chemistry vol. 26, No. 6, 2000, pp. 559-565.*

* cited by examiner

*Primary Examiner* — Hezron E Williams
*Assistant Examiner* — Nathaniel Kolb
(74) *Attorney, Agent, or Firm* — Oliff & Berridge, PLC

(57) ABSTRACT

Disclosed a test management method for an indentation tester which includes a control section and forms an indentation on a surface of a heated or cooled sample by pressing an indenter to which a load is applied onto the surface of the sample, the test management method including the steps of: measuring a predetermined reference block as the sample under a plurality of temperature environments to obtain a test result; calculating a test error caused by temperature environment based on the test result by the control section; and judging whether or not the test error is within a predetermined range by the control section.

4 Claims, 11 Drawing Sheets

TEST MANAGEMENT METHOD FOR INDENTATION TESTER AND INDENTATION TESTER

BACKGROUND OF THE INVENTION

1. Field of the Invention

The present invention relates to a test management method for an indentation tester, and an indentation tester.

2. Description of Related Art

There has been conventionally known, as a material tester, for example, an indentation tester to form an indentation on a sample surface by pressing an indenter shaft thereonto to measure a physicality value such as a hardness of material. Specifically, for example, the indentation tester measures an indentation depth (an amount of displacement of the indenter shaft) at the time of when a tip of the indenter is pressed onto the sample surface, by a displacement gauge, and obtains a relation between the measured the indentation depth and a test force (burden load) at the time of when the indenter shaft is pressed onto the sample surface to measure a physicality value such as a hardness of sample.

By the way, plastic, thin film material and the like presently become necessary component materials for various machines and structural objects. In recently years, since these materials are often used in a high temperature environment, a request for monitoring a material characteristic at high temperature to help a material development or evaluation has increased.

On the other hand, an instrumented indentation test is most suitable for evaluating plastic or thin film material, which instrumented indentation test is a kind of an indentation hardness test such as Vickers, and measures the test force and the indentation depth point by point in an indentation process so as to obtain various mechanical characteristics of material by analyzing an obtained curve of the test force vs. the indentation depth. An investigation of standardization of a testing method has been promoted, so that a recognizability of the instrumented indentation test has been increased. In particular, the instrumented indentation test according to which the indentation is small is called a nano-indentation or an ultra-micro hardness test, and attracts an attention as a thin film evaluation method.

In order to respond to above request, for example, a sample stage heater (a sample heating device) for heating a sample stage is attached to an instrumented indentation tester, and the sample stage heater heats the sample stage to heat the sample placed on the sample stage.

In the indentation tester, which is not limited to the instrumented indentation tester, to which the sample stage heater is attached, since an indenter shaft contacts with the heated sample or the heated sample stage heats an air around the sample stage, during testing the sample and the like, the indenter shaft is also heated to be thermally-expanded. Moreover, constructional components (a tester frame and the like) of the indentation tester are also thermally-expanded by an influence of high temperature atmosphere. There is a problem that an accurate value (a measurement value) of the indentation depth cannot be obtained when the indenter shaft or the constructional components of the indentation tester are thermally-expanded.

Therefore, for example, there is proposed an indentation tester including: an indenter shaft; a doubly supported beam to the central portion of which the indenter is attached; and a doubly supported beam supporting portion to support the doubly supported beam, wherein at least one of the doubly supported beam and the doubly supported beam supporting portion which are constructional components of the indentation tester is composed of material (specifically, Super Invar) having a small thermal expansion coefficient, and the like (for example, see Japanese Patent Application Laid-Open Publications No. 2004-012178).

Moreover, for example, there is also proposed a method including connecting a stretchable container with a container in an introduction portion, which stretchable container contains: a holding portion (the sample stage) to hold a sample; a heating portion (the sample stage heater) to heat the sample; and an indenter portion, under an inactive gas atmosphere, and which container contains: a loading mechanism to give the burden load to a sample; a load measuring member to measure the load; and a displacement gauge to measure an amount of the indentation of the sample by the load, to reduce a heat influence of a heat conduction or a heat convection from a heat source of the sample stage heater for heating the sample to the loading mechanism or the displacement gauge so as to reduce a heat influence to the value of the indentation depth (the measurement value) (for example, see Japanese Patent Application Laid-Open Publications No. 2002-181679).

However, even in the case of forming the indenter shaft by material having small thermal expansion coefficient or forming the constructional components of the indentation tester by material having small thermal expansion coefficient, the indenter and the constructional components expand with heat to no small extent. Moreover, since an extent of the heat expansion is not known, it is impossible to judge whether or not the measurement value is reliable.

Moreover, even in a case like Japanese Patent Application Laid-Open Publications No. 2002-181679 that the sample stage, the sample stage heater and the indenter are contained in different container from that in which the loading mechanism, the load measuring member, and the displacement gauge are contained, it is impossible to suppress the heat expansion of the sample stage or the indenter (indenter shaft). Furthermore, since an extent of heat expansion is not known, it is impossible to judge whether or not the measurement value is reliable.

SUMMARY OF THE INVENTION

An object of the present invention is to provide a test management method for an indentation tester for ensure a reliability of a measurement value measured by an indentation tester, and an indentation tester which can ensure the reliability of the measurement value.

According to a first aspect of the present invention, a test management method for an indentation tester which includes a control section and forms an indentation on a surface of a heated or cooled sample by pressing an indenter to which a load is applied onto the surface of the sample includes the steps of: measuring a predetermined reference block as the sample under a plurality of temperature environments to obtain a test result; calculating a test error caused by temperature environment based on the test result by the control section; and judging whether or not the test error is within a predetermined range by the control section.

According to a second aspect of the present invention, a test management method for an indentation tester which includes a control section and forms an indentation on a surface of a heated or cooled sample by pressing an indenter to which a load is applied onto the surface of the sample includes the steps of: measuring a predetermined reference block as the sample under a plurality of temperature environments to obtain a test result; calculating a test error caused by temperature environment based on the test result by the control section; and correcting the test result of the sample except the reference block based on the test error by the control section.

According to a third aspect of the present invention, an indentation tester to form an indentation on a surface of a heated or cooled sample by pressing an indenter to which a load is applied onto the surface of the sample includes: a reference block measurement member to measure a predetermined reference block as the sample under a plurality of temperature environments to obtain a test result; a calculation member to calculate a test error caused by a heat expansion of the whole indentation tester depending on a sample temperature based on the test result; and a judgment member to judge whether or not the test error is within a predetermined range.

According to a fourth aspect of the present invention, an indentation tester to form an indentation on a surface of a heated or cooled sample by pressing an indenter to which a load is applied onto the surface of the sample includes: a reference block measurement member to measure a predetermined reference block as the sample under a plurality of temperature environments to obtain a test result; a calculation member to calculate a test error caused by a heat expansion of the whole indentation tester depending on a sample temperature based on the test result; and a correction member to correct the test result of the sample except the reference block based on the test error.

BRIEF DESCRIPTION OF THE DRAWINGS

The present invention will become more fully understood from the detailed description given hereinbelow and the appended drawings which given by way of illustration only, and thus are not intended as a definition of the limits of the present invention, and wherein.

DETAILED DESCRIPTION OF THE INVENTION

In the following, the preferred embodiment for implementing the present invention will be described in detail with reference to the drawings. Incidentally, the scope of the present invention is not limited to examples shown in the drawings.

[Whole Construction of Indentation Tester]

An indentation tester 100 of the present invention includes, for example, a control section 200, and forms an indentation on a surface of a heated or cooled sample S by pressing an indenter 4, to which the load is applied, onto the surface of the sample S.

Specifically, the indentation tester 10 is an instrumented indentation tester to which a heating/cooling device 3 as a heating/cooling mechanism to heat/cool the sample S is attached.

Figure 1:
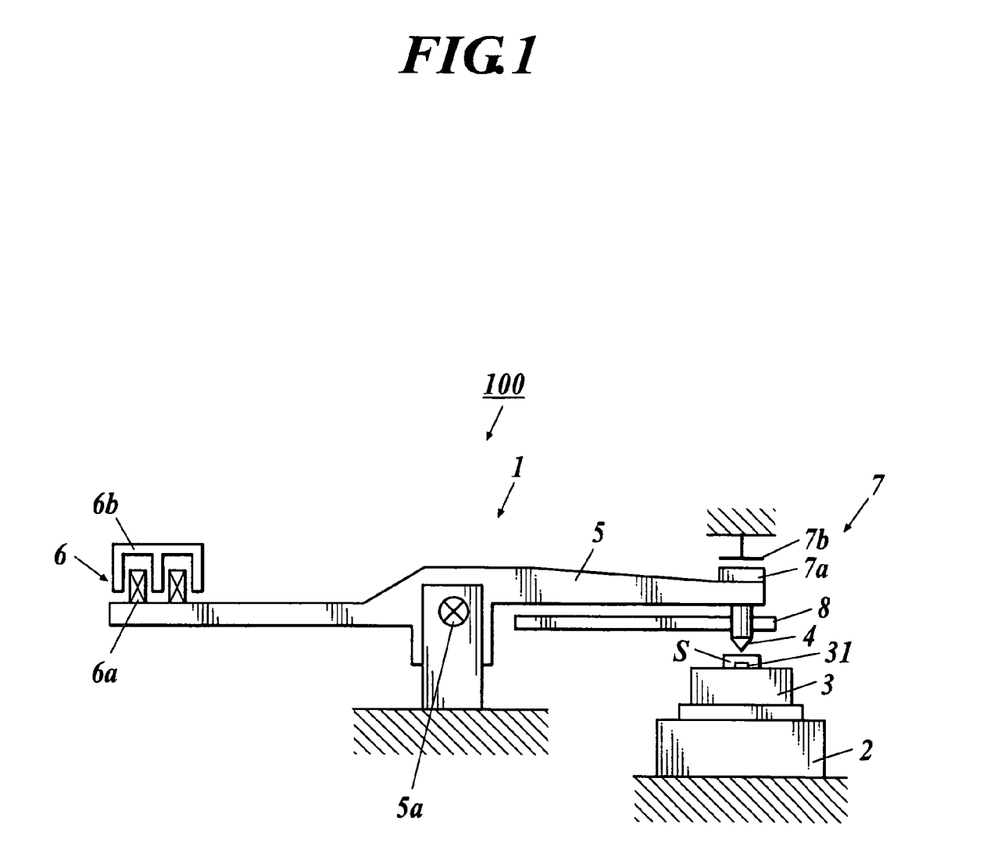
FIG. 1 is a side view showing a cross section of a part of an indentation tester according to the present invention.
Figure 2:
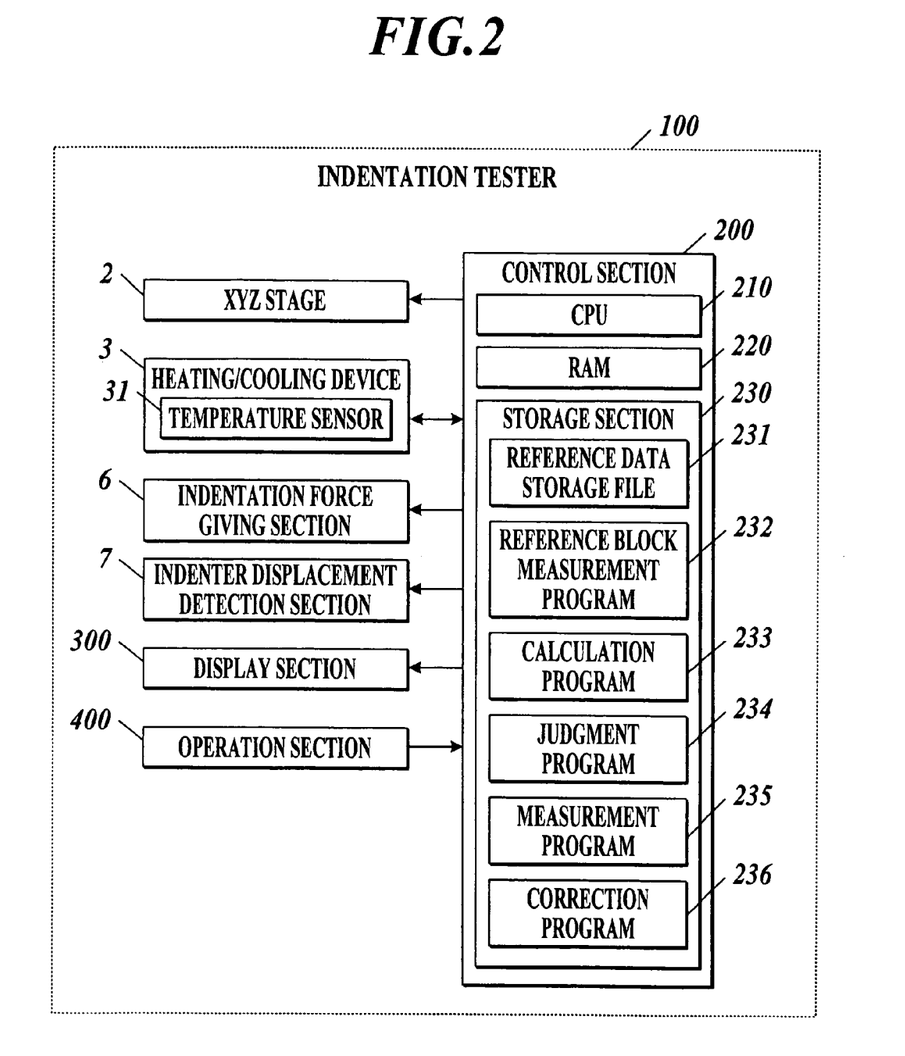
FIG. 2 is a block diagram showing a main construction of the indentation tester of FIG. 1.

More specifically, the indentation tester 100 includes, for example, as shown in FIGS. 1 and 2, the control section 200 and a testing device body 1 in which each constructional component is arranged. The testing device body 1 includes: an XYZ stage 2 to move the sample S in X, Y, and Z directions; the heating/cooling device 3 to heat/cool the sample S; a loading lever 5 one end of which having the indenter 4 for forming the indentation on the sample S; an indentation force giving section 6 to give a predetermined indentation force to the loading lever 5; an indenter displacement detection section 7 to detect a displacement of the indenter 4; a heat shielding section 8 to reduce a heat influence from the heating/cooling device 3 to the loading mechanism (loading lever 5 and the like) or to the indenter displacement detection section 7; a display section 300; a operation section 400; and the like. (XYZ stage) The XYZ stage 2 is configured to move in X, Y, and Z directions (namely a horizontal direction and a vertical direction), for example, according to a control signal input from the control section 200. The heating/cooling device 3 is placed on the XYZ stage 2, and the XYZ stage 2 moves the heating/cooling device 3 in X, Y and Z directions to move the sample S placed on the heating/cooling device 3 in X, Y and Z directions.

(Heating/Cooling Device)

The heating/cooling device 3 is placed on the XYZ stage 2, and is configured to heat or cool the sample S placed on the heating/cooling device 3, for example, according to a control signal input from the control section 200.

The control section 200 applies current to the heating/cooling device 3 when the sample S is heated or cooled, for example. Specifically, for example, a temperature sensor 31 is provided in the vicinity of the sample S in the heating/cooling device 3, and the control section 200 controls the current apply based on a temperature detected by the temperature sensor 31 so that the heating/cooling device 3 heats or cools the sample S at the proper temperature.

(Loading Lever)

The loading lever 5 is formed in rod-like shape for example, and a near center portion of which is fixed on a base through a cross spring 5a.

The indenter 4 is provided at one end of the loading lever 5 to be capable of approaching to or separating from the surface of the sample S from above the sample S placed on the heating/cooling device 3, the indenter 4 forming the indentation on the surface of the sample S by being pressed thereto.

Moreover, a force coil 6a which constructs the indentation force giving section 6 is provided at the other end of the loading lever 5.

(Indentation Force Giving Section)

The indentation force giving section 6 is a force motor, for example, and includes the force coil 6a attached to the loading lever 5, a stationary magnet 6b fixed so as to face the force coil 6a, and so on.

The indentation force giving section 6 turns the loading lever 5, for example, by using a force generated by an electromagnetic induction caused by a magnetic field produced in a gap by the stationary magnet 6b and current flowing through the force coil 6a set in the gap, according to a control signal input from the control section 200. This allows an end of the loading lever 5 on the indenter 4 side to fall so that the indenter 4 is pressed onto the sample S.

(Indenter Displacement Detection Section)

The indenter displacement detection section 7 is a capacitance type displacement sensor, for example, and includes a movable plate 7a provided at the end of the loading lever 5 on the indenter 4 side, a fixed plate 7b fixed so as to face the movable plate 7a, and the like.

The indenter displacement detection section 7 detects a displacement amount (an indentation depth at the time when the indenter 4 is pressed onto the sample S) of the indenter 4's movement at the time of when the indenter 4 forms the indentation on the sample S, for example, by detecting a change of a capacitance between the movable plate 7a and the fixed plate 7b. Then, the indenter displacement detection section 7 outputs a displacement signal based on the detected displacement amount to the control section 200.

Incidentally, though the capacitance type displacement sensor is quoted as an example of the indenter displacement detection section 7, it is not limited to the above, and can be an optical displacement sensor or an eddy current displacement sensor, for example.

(Heat Shielding Section)

The heat shielding section 8 is provided for reducing a heat influence of heat conduction or heat convection from the heating/cooling device 3 to the loading mechanism (the loading lever 5 and the like) or to the indenter displacement detection section 7, and is placed, for example, between the heating/cooling device 3 and the loading lever 5.

(Display Section)

The display section 300 is composed of a Liquid Crystal Display (LCD) panel and the like, for example, and performs given displaying process according to a display signal input from the control section 200.

(Operation Section)

The operation section 400 is composed of operation keys and the like, for example, and outputs an operation signal associated with the operation to the control section 200 when a user operates the operation section 400. Moreover, the operation section 400 may include other operation devices such as pointing devices including a mouse and a touch panel, and remote controller, as appropriate.

Specifically, the operation section 400 is operated, for example, when a user instructs to store reference data.

Moreover, the operation section 400 is operated, for example, when a user instructs to perform maintenance of the indentation tester 100.

Furthermore, the operation section 400 is operated, for example, when a user instructs to perform an indentation test by using the sample S other than a reference block. In this case, the user specifies a desirable sample temperature by operating the operation section 400.

(Control Section)

The control section 200 controls each section of the indentation tester 100 and manages an evaluation of material characteristics of the sample S by the indentation tester 100, for example.

Specifically, the control section 200 is configured to include, for example, as shown in FIG. 2, a Central Processing unit (CPU) 210, a Random Access Memory (RAM) 220, a storage section 230, and the like. The control section 200 is connected to the XYZ stage 2, the heating/cooling device 3, the indentation force giving section 6, the indenter displacement detection section 7, the display section 300, the operation section 400 and the like, through a system bus, a driving circuit, and the like.

The CPU 210 performs various control operations according to various processing programs for the indentation tester 100 stored in the storage section 230, for example.

The RAM 220 includes a program storage area for expanding a processing program to be executed by the CPU 210, and a data storage area for storing input data, a processing result generated as executing the processing program, and the like, for example.

The storage section 230 stores a system program executable in the indentation tester 100, various processing programs executable by the system program, data to be used when the various processing programs are executed, data of processing result arithmetic-processed by the CPU 210, and the like, for example. Incidentally, the programs are stored in the stored section 230 in the form of a computer-readable program code.

Specifically, the storage section 230 stores a reference data storage file 231, a reference block measurement program 232, a calculation program 233, a judgment program 234, a measurement program 235, a correction program 236, and the like, for example.

The reference data storage file 231 stores reference data (data indicating a degree of a heat expansion of the whole indentation tester 100 (described below)) generated by the CPU 210 executing the calculation program 233, for example.

The reference block measurement program 232 allows the CPU 210 to realize a function to measure a predetermined reference block as the sample S under a plurality of temperature environments to obtain a test result, for example.

Here, the reference block is, for example, preferably formed by material the degree of the heat expansion of which is vanishingly small in comparison with that of the whole indentation tester 100, more preferably composed of any one of fused quartz, single crystal quartz, ceramics, single crystal alumina, and low thermal expansion alloy, and most preferably composed of any one of fused quartz and single crystal quartz which have relatively-low hardness.

Specifically, the CPU 210 controls the heating/cooling device 3 so that the reference block placed on the heating/cooling device 3 has a predetermined sample temperature, and controls the indentation force giving section 6 so that a predetermined test force is given to the reference block placed on the heating/cooling device 3, based on a predetermined operation condition (for example, operation conditions of the heating/cooling device 3 and the indentation force giving section 6) previously set for performing the indentation test by using the reference block, when the operation signal for instructing to store the reference data or the operation signal for instructing to perform maintenance of the indentation tester 100 is input from the operation section 400, for example. Then, the CPU 210 measures the indentation depth by the indenter in the sample S and the test force at the time of forming the indentation point by point to measure the curve of the test force vs. the indentation depth, for example.

A method of indentation test for the reference block by the indentation tester 100 in order to measure the curve of the test force vs. the indentation depth will be explained more specifically.

First, the reference block is placed on the heating/cooling device 3 placed on the XYZ stage 2.

Next, the CPU 210 heats or cools the reference block by the heating/cooling device 3. The CPU 210 controls heating/cooling of the heating/cooling device 3 based on the temperature detected by the temperature sensor 31 at that time.

Next, the CPU 210 applies current depending on a predetermined test force to the force coil 6a of the indentation force giving section 6 so as to allow the indentation force giving section 6 to operate.

This allows the indentation force giving section 6 to give a predetermined force to the loading lever 5 to rotate the loading lever 5 in the clockwise direction so that the indenter 4 is pressed onto the surface of the sample S from above the sample S to form the indentation on the surface of the sample S.

During forming the indentation, the load applied to the indenter 4 is increased gradually until reaching a set maximum test force, by rotating the loading lever 5 in the clockwise direction (loading period).

Figure 3A:
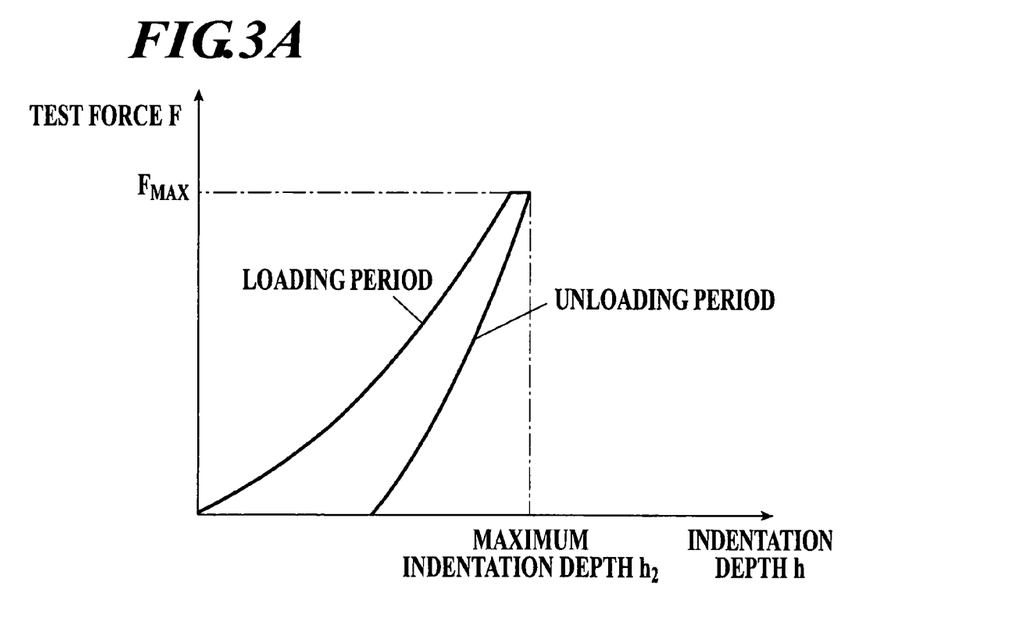
FIGS. 3A and 3B are views showing a relation between a test force and an indentation depth at the time of when an indentation test is performed by the indentation tester of the present invention.

In the loading period, as shown in the curve of the test force F vs. the indentation depth h of FIG. 3A, the indentation depth by the indenter 4 in the sample S is increased by increasing the test force applied to the indenter 4.

Next, the CPU 210 controls an amount of current supply to the force coil 6a to allow the indentation force giving section 6 to operate so as to remove the load of the loading lever 5, in order to gradually decrease the load applied to the indenter 4, when the CPU 210 judges that the load applied to the indenter 4 reaches the maximum test force. This decreases the load applied to the indenter 4 gradually (unloading period).

In the unloading period, as shown in the curve of the test force F vs. the indentation depth h of FIG. 3A, the indentation depth by the indenter 4 in the sample S is decreased by decreasing the test force applied to the indenter 4.

Such a method can perform the indentation test for the reference block by the indentation tester 100.

Then, the CPU 210 performs the indentation test for the above-described reference block under a plurality of the temperature environments to obtain the test result under a plurality of the temperature environments, namely the curve of the test force vs. the indentation depth under a plurality of the temperature environments. Here, a plurality of the temperature environments includes environments under room temperature, and environments under higher/lower temperature than an room temperature, for example.

The CPU 210 functions as a reference block measurement member by executing the reference block measurement program 232.

The calculation program 233 allows the CPU 210 to realize a function to calculate a test error caused by temperature environment, namely a test error caused by the heat expansion of the whole indentation tester 100 depending on the temperature of the sample S (reference block), based on the test result obtained by the CPU 210 executing the reference block measurement program 232, for example.

Specifically, the CPU 210 calculates a test error caused by the heat expansion of the whole indentation tester 100 to generate the data indicating the degree of the heat expansion of the whole indentation tester 100, based on the test result obtained by the CPU 210 executing the reference block measurement program 232, for example.

More specifically, the CPU 210 obtains the test error, namely a difference ($\Delta$) of a maximum indentation depth from that at room temperature, based on the curve of the test force vs. the indentation depth under a plurality of the temperature environments.

Figure 4A:
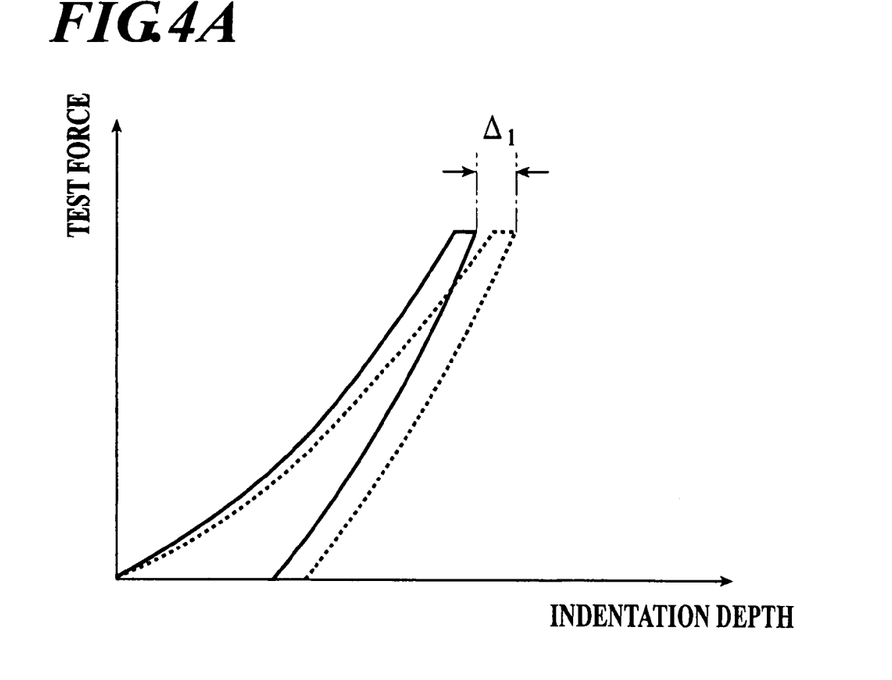
FIGS. 4A and 4B are views for explaining a test error (a difference of a maximum indentation depth from that at room temperature)
Figure 4B:
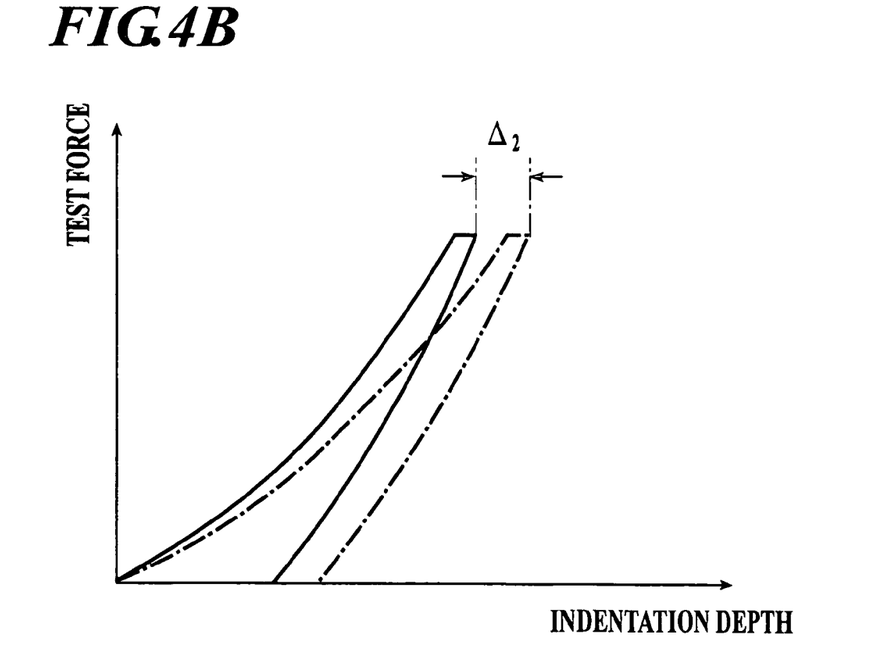

Here, the maximum indentation depth is, for example, as shown in FIG. 3A, the indentation depth h at the time of when the test force F is a maximum value, namely the indentation depth at the time of when the process is shifted to the unloading period. For example, as shown in FIG. 4A where the curve of the test force vs. the indentation depth at room temperature is shown by continuous line and the curve of the test force vs. the indentation depth at higher temperature $T_1$ than the room temperature is shown by broken line, the difference ($\Delta$) of the maximum indentation depth at $T_1$ from that at the room temperature is $\Delta_1$. Moreover, for example, as shown in FIG. 4B where the curve of the test force vs. the indentation depth at room temperature is shown by continuous line and the curve of the test force vs. the indentation depth at higher temperature $T_2$ (for example, $T_2 > T_1$) than the room temperature is shown by chain line, the difference ($\Delta$) of the maximum indentation depth at $T_2$ from that at the room temperature is $\Delta_2$.

Figure 5:
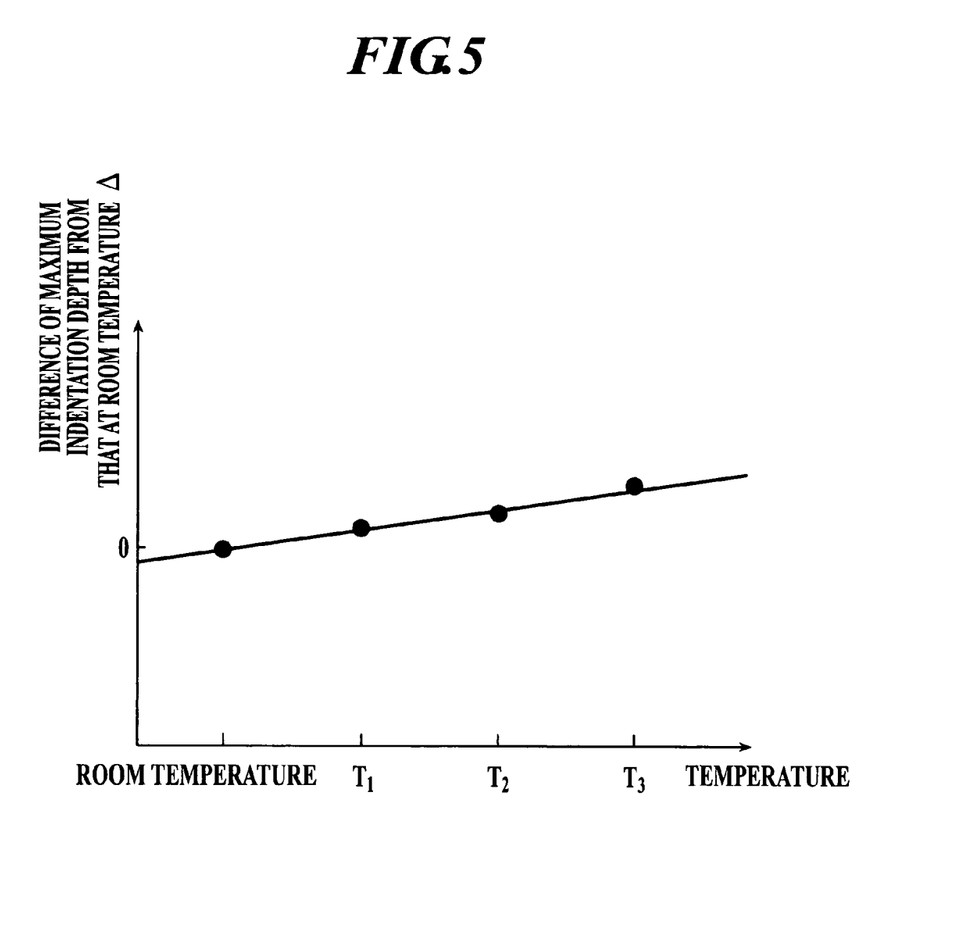
FIG. 5 is a view showing data indicating a degree of heat expansion of the whole indentation tester.

Next, the CPU 210, for example, as shown in FIG. 5, plots the difference ($\Delta$) of the maximum indentation depth at each temperature from that at room temperature to generate the data indicating the degree of the heat expansion of the whole indentation tester 100. Then, when the operation signal for instructing to store the reference data is input from the operation section 400 and the CPU 210 generates the data indicating the degree of the heat expansion of the whole indentation tester 100, the CPU 210 allows the reference data storage file 231 to store the data as the reference data.

Incidentally, though FIG. 5 shows the data indicating the degree of the heat expansion of the whole indentation tester 100, which is developed by plotting the difference ($\Delta$) of the maximum indentation depth from that at room temperature, at each temperature from an room temperature to a higher temperature than the room temperature, the data indicating the degree of the heat expansion of the whole indentation tester 100 may be a data developed by plotting the difference ($\Delta$) of the maximum indentation depth from that at room temperature, at each temperature from a lower temperature than an room temperature to the room temperature, or a data developed by plotting the difference ($\Delta$) of the maximum indentation depth from that at room temperature, at each temperature from a lower temperature than an room temperature to a higher temperature than the room temperature.

Figure 3B:
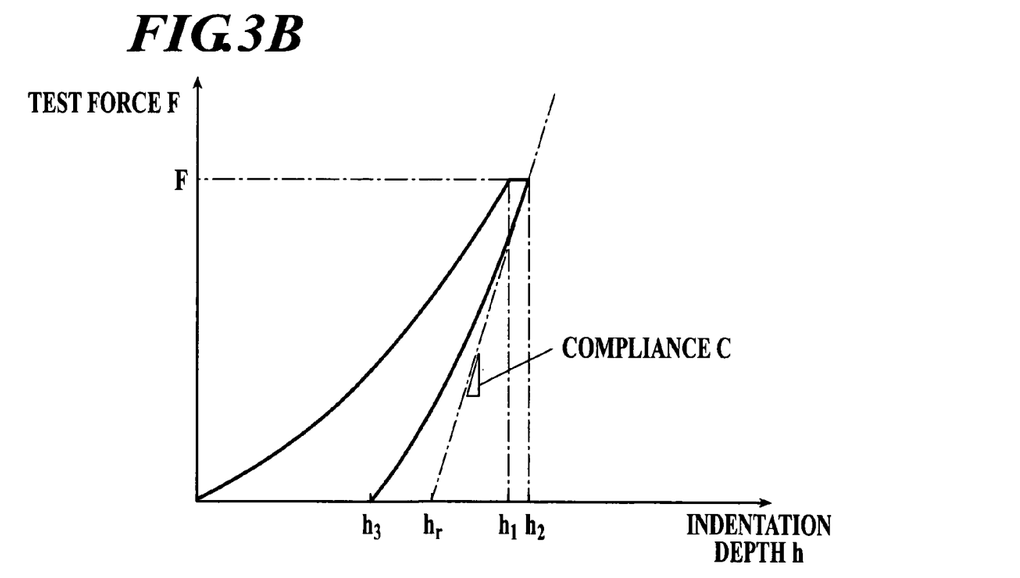

Moreover, though the test error is the difference ($\Delta$) of the maximum indentation depth ($h_2$) from that at room temperature, it is not limited to the above. The test error may be any differences of parameters from those at room temperature, the parameters being obtained from the curve of the test force vs. the indentation depth. As the parameter obtained from the curve of the test force vs. the indentation depth, for example, there can be quoted $h_1$, $h_3$, $h_r$, a compliance C ($=d(h_2-h_r)/dF$) and the like which are shown in FIG. 3B. The compliance C is a slope of initial unloading. Furthermore, as the parameter obtained from the curve of the test force vs. the indentation depth, for example, there can be quoted a parameter defined by the standard (ISO14577) (Martens hardness (HM: hardness for deformations including an elastic deformation and a plastic deformation (calculated from maximum indentation depth), $HM_S$: hardness for deformations including an elastic deformation and a plastic deformation (calculated from a load curve (the curve of the test force vs. the indentation depth))), an indenting hardness ($H_{IT}$: hardness for a plastic deformation (associated with conventional Vickers hardness)), an indentation creep ($C_{IT}$: a proportion of a creep deformation amount in a total deformation amount), an indentation coefficient ($E_{IT}$: an elastic coefficient (a longitudinal elastic coefficient, associated with Young's modulus)), an indentation power ($\eta_{IT}$: a proportion of a elastic deformation in a total amount of mechanical work during an indentation process)

and the like), a parameter uniquely adapted by the indentation tester 100, and a parameter uniquely adapted by a user.

In addition, though FIG. 5 shows the data indicating the degree of the heat expansion of the whole indentation tester 100 with an approximate straight line (a primary expression), the data indicating the degree of the heat expansion of the whole indentation tester 100 may be shown with an approximate curve line (a quadratic expression).

Moreover, a data indicating the degree of the heat expansion of the whole indentation tester 100 to which an error bar is added may be the data indicating the degree of the heat expansion of the whole indentation tester 100.

Figure 6:
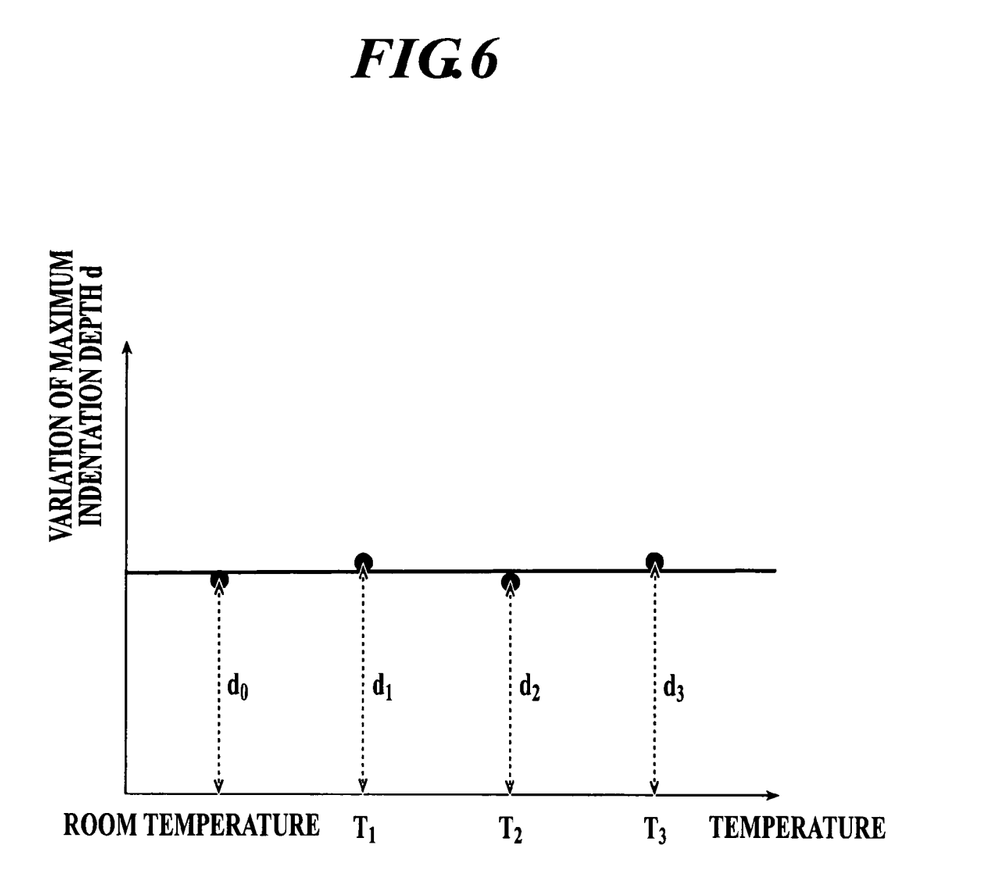
FIG. 6 is a view showing variation data with regards to a variation rate or magnitude of the maximum indentation depth.
Figure 7:
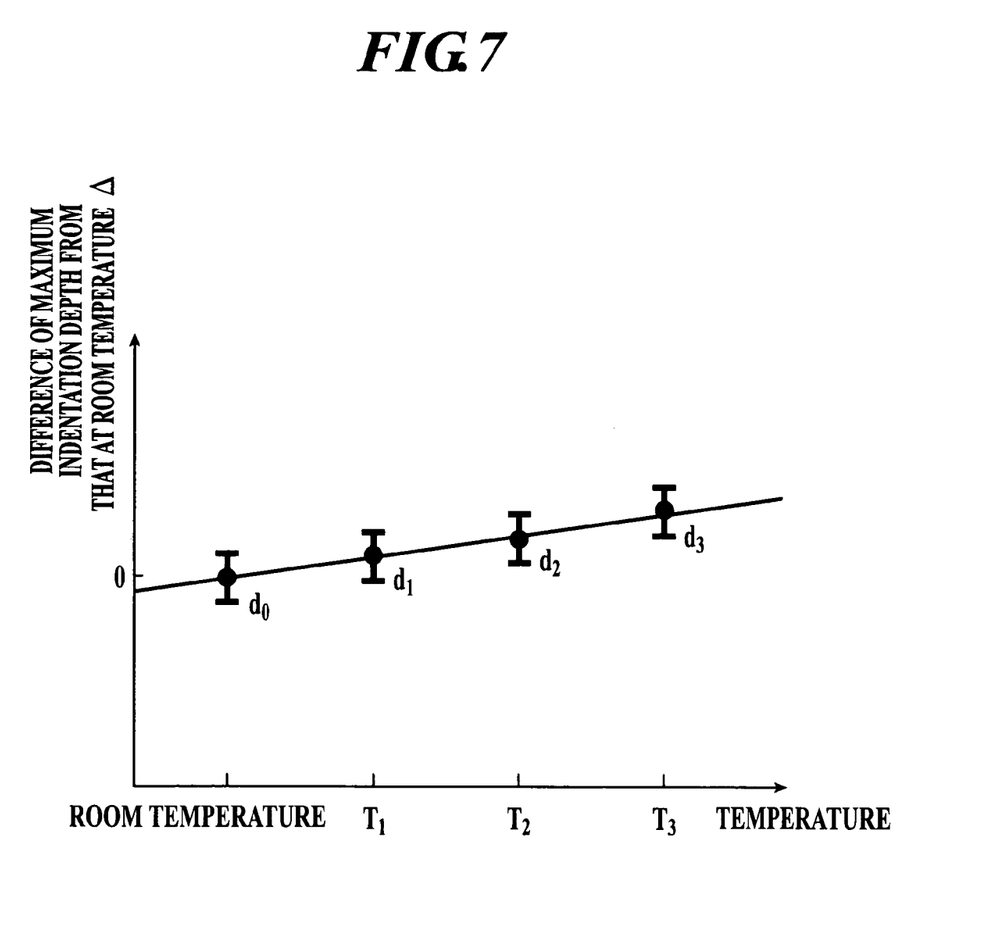
FIG. 7 is a view showing data, to which an error bar is added, indicating a degree of heat expansion of the whole indentation tester.

Specifically, the CPU 210 executes, for example, the reference block measurement program 232 to repeat performing the above-mentioned indentation test for the reference block at same temperature so as to measure a plurality of the curves of the test force vs. the indentation depth at each temperature. Then, the CPU 210 executes, for example, the calculation program 233 to obtain the magnitude of variation (d) of the maximum indentation depth at each temperature based on these curves of the test force vs. the indentation depth so as to develop variation data by plotting the magnitude of variation (d) of the maximum indentation depth at each temperature as shown in FIG. 6. Next, the CPU 210 add the error bar indicating the variation magnitude (FIG. 6) of the maximum indentation depth to data indicating the degree of the heat expansion of the whole indentation tester 100 which is developed by plotting an average value of the difference ($\Delta$) of the maximum indentation depth at each temperature from that at room temperature, for example, as shown in FIG. 7, to allow the above data to be the data indicating the degree of the heat expansion of the whole indentation tester 100.

The data indicating the degree of the heat expansion of the whole indentation tester 100 generated in this way may be used for giving a user the degree of the heat expansion of the whole indentation tester 100 on the presumption that the reference block does absolutely not expand with heat.

Moreover, the data indicating the degree of the heat expansion of the whole indentation tester 100 may be used as an indicator of the maintenance of the indentation tester 100 by comparing the data previously stored in the reference data storage file 231 with the data generated when the operation signal for instructing to perform the maintenance of the indentation tester is input from the operation section 400.

The CPU 210 functions as the calculation member by executing the calculation program 233.

The judgment program 234 allows the CPU 210 to realize a function to judge whether or not the test error calculated by the CPU 210 executing the calculation program 233 is within a predetermined range.

Specifically, the CPU 210 judges whether or nor the test error caused by the heat expansion of the whole indentation tester 100 depending on the temperature of the sample S (reference block) is within a predetermined range, for example, by comparing the reference data (the data indicating the degree of the heat expansion of the whole indentation tester 100) previously stored in the reference data storage file 231 with the data indicating the degree of the heat expansion of the whole indentation tester 100 which is generated when the operation signal for instructing to perform the maintenance of the indentation tester 100 is input from the operation section 400.

Then, the CPU 210 allows the display section 300 to display the judgment result, for example.

More specifically, the CPU 210 determines the predetermined range based on the reference data (the data indicating the degree of the heat expansion of the whole indentation tester 100) previously stored in the reference data storage file 231, and then judges whether or not the data indicating the degree of the heat expansion of the whole indentation tester 100 which is generated when the operation signal for instructing to perform the maintenance of the indentation tester 100 is input from the operation section 400 is within the determined predetermined range, for example.

Figure 8:
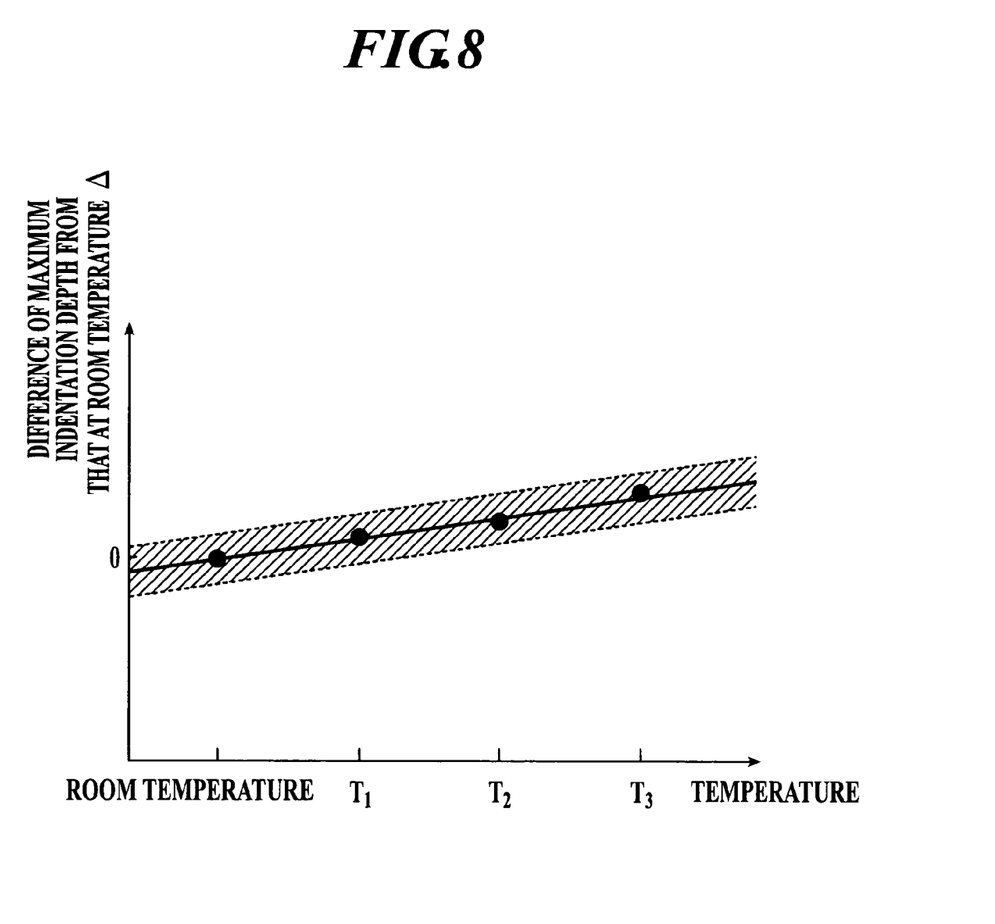
FIG. 8 is a view for explaining about a predetermined range.

Here, the predetermined range may be, for example, a range within plus/minus several percent from the reference data (the data indicating the degree of the heat expansion of the whole indentation tester 100 (for example, FIG. 5)), previously stored in the reference data storage file 231, like a range marked with diagonal lines in FIG. 8, or may be, for example, a range within the error bar of the reference data (the data (for example, FIG. 7) indicating the degree of the heat expansion of the whole indentation tester 100) previously stored in the reference data storage file 231.

The CPU 210 functions as judgment member by the executing the judgment program 234.

The measurement program 235 allows the CPU 210 to realize a function to obtain the test result of the sample S except the reference block, for example.

Specifically, the CPU 210 controls the heating/cooling device 3 so that the sample S placed on the heating/cooling device 3 reaches user's desirable sample temperature, and controls the indentation force giving section 6 to give a predetermined test force onto the sample S placed on the heating/cooling device 3, based on a predetermined operation condition (for example, the operation condition of the heating/cooling device 3 or the indentation force giving section 6) previously set for performing the indentation test by using the sample S except the reference block, when the operation signal for instructing to perform the indentation test by using the sample S except the reference block is input from the operation section 400, for example. Then, the CPU 210 measures the indentation depth by the indenter 4 in the sample S during forming the indentation and the test force during forming the indentation point by point to measure the curve of the test force vs. the indentation depth, for example.

Incidentally, the detailed explanation about the method of indentation test for the sample S except the reference block by the indentation tester 100 in order to measure the curve of the test force vs. the indentation depth is omitted, because it is same as the above-described method of the indentation test for the reference block by the indentation tester 100, except in the points that the sample S placed on the heating/cooling device 3 is the sample except the reference block, and that the temperature of the sample S is user's desirable sample temperature.

The correction program 236 allows the CPU 210 to realize a function to correct the test result for the sample S except the reference block which is measured by the CPU 210 executing the measurement program 235, based on the test error calculated by the CPU 210 executing the calculation program 233, for example.

Specifically, the CPU 210 corrects the curve of the test force vs. the indentation depth of the sample S except the reference block which is measured by the CPU 210 executing the measurement program 235, based on the reference data (the data indicating the degree of the heat expansion of the whole indentation tester 100) previously stored in the reference data storage file 231, for example.

Then, the CPU 210 allows the display section 300 to display the correction result, for example.

Here, the curve of the test force vs. the indentation depth of the sample S except the reference block is corrected on the presumption that the reference data previously stored in the reference data storage file 231 is the data indicating only the degree of the heat expansion of the whole indentation machine 100.

Since the degree of the heat expansion of the reference block is small, the hardness of the reference block at high (low) temperature is substantively same as the hardness at room temperature, and the shape of the curve of the test force vs. the indentation depth does not change even if the temperature changes. However, since the whole indentation tester 100 is influenced by the temperature, the shape of the curve of the test force vs. the indentation depth obtained by the indentation test using the reference block changes due to the influence if the temperature changes. Therefore, the reference data previously stored in the reference data storage file 231 is the data indicating only the degree of the heat expansion of the whole indentation tester 100, and it is decided to perform the correction of the curve of the test force vs. the indentation depth of the sample S except the reference block by using this reference data.

More specifically, the CPU 210 obtains the degree of the heat expansion of the whole indentation tester 100, for example, from the reference data (the data indicating the degree of the heat expansion of the whole indentation tester 100) previously stored in the reference data storage file 231. Next, the CPU 210 subtract the obtained degree from the indentation depth by the indenter 4 in the sample S during forming the indentation on the sample S except the reference block to correct the curve of the test force vs. the indentation depth of the sample S except the reference block.

Moreover, the CPU 210 calculates the hardness of the sample S, based on the corrected curve of the test force vs. the indentation depth and a previously-set calculation expression of hardness corresponding to the indentation test, for example.

The CPU 210 functions as a correction member by executing the correction program 236.

[Test Management Method for Indentation Tester]

Figure 9:
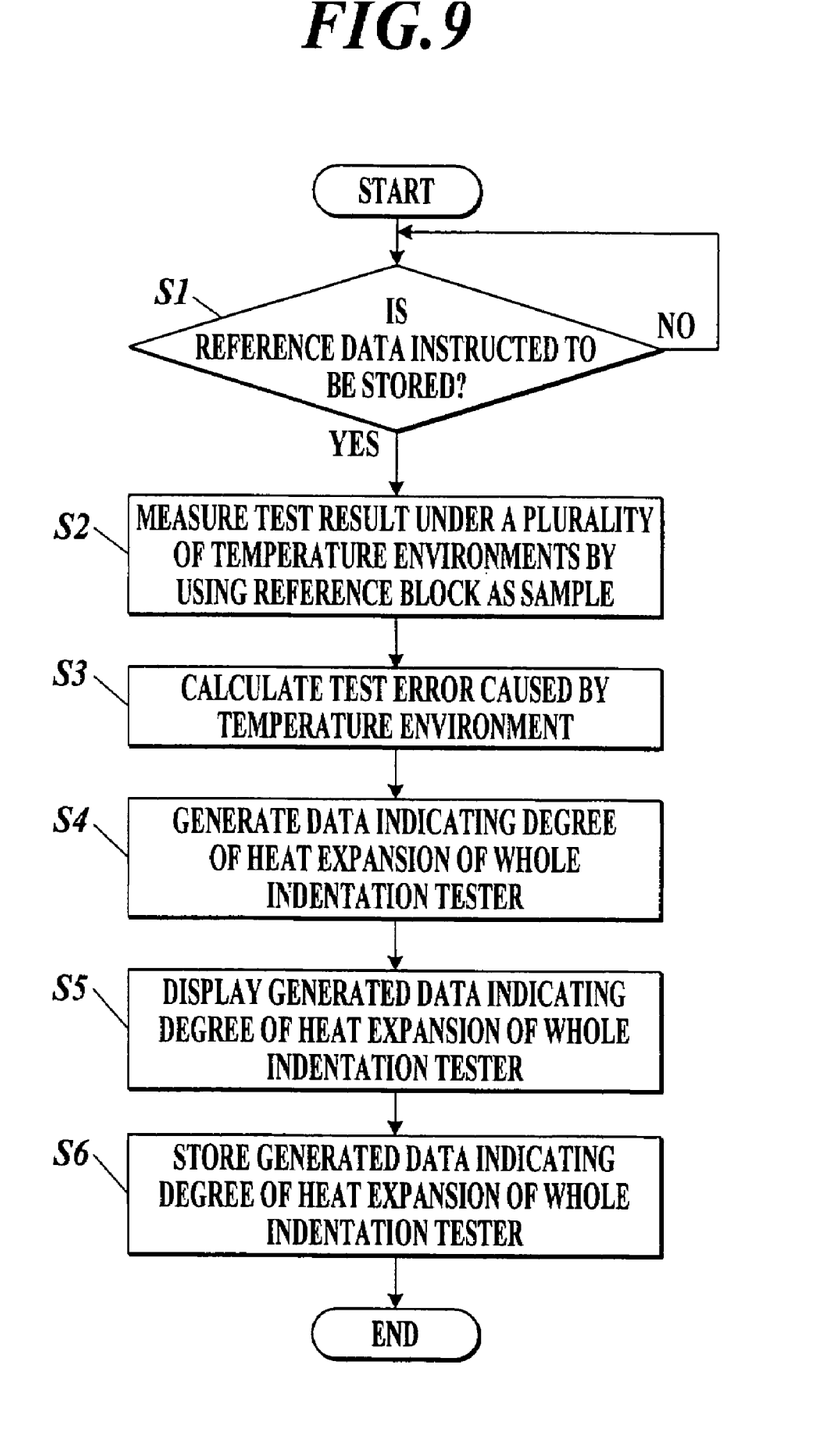
FIG. 9 is a flow chart for explaining a process of storing reference data by the indentation tester.
Figure 10:
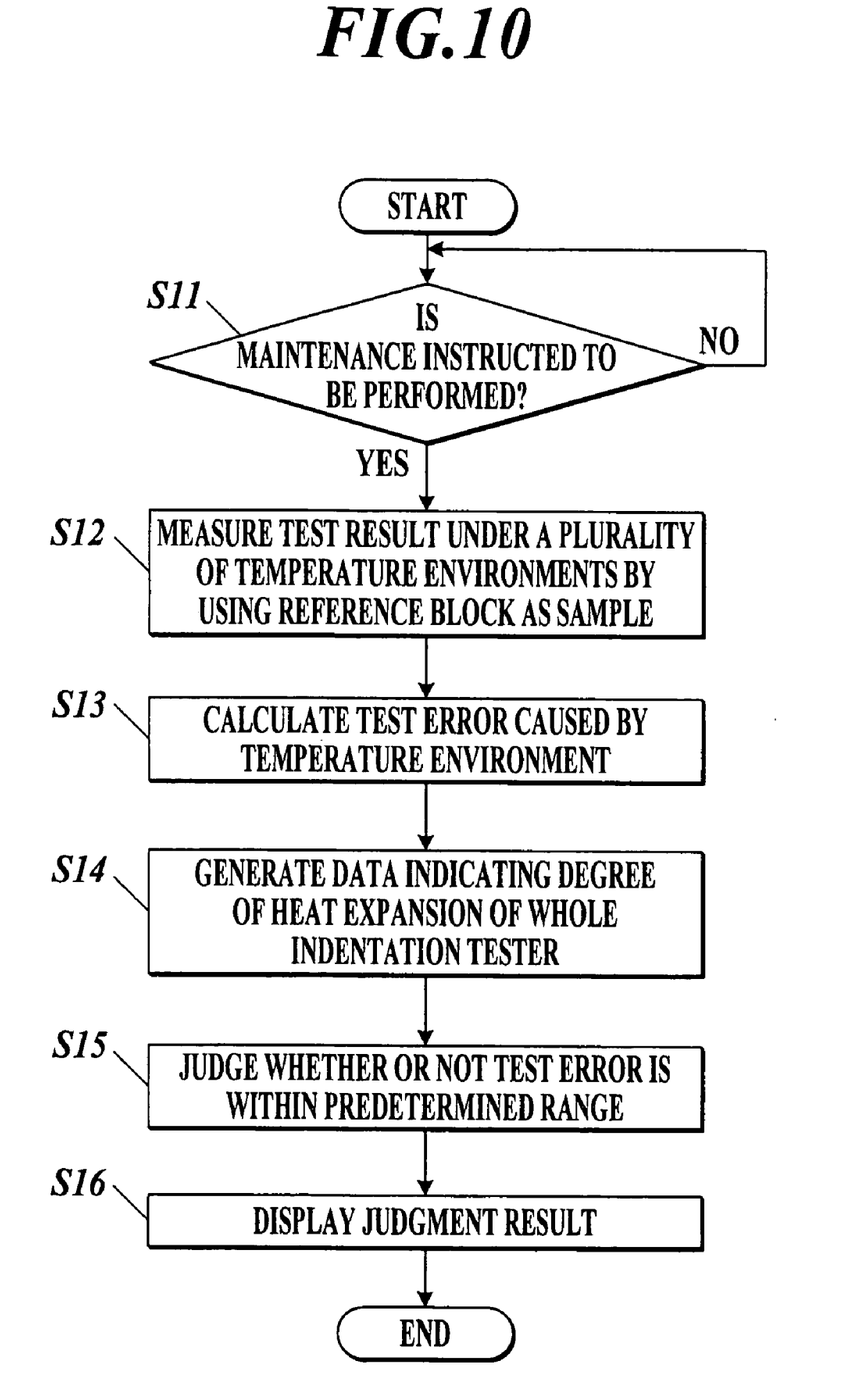
FIG. 10 is a flow chart for explaining a maintenance process by the indentation tester.
Figure 11:
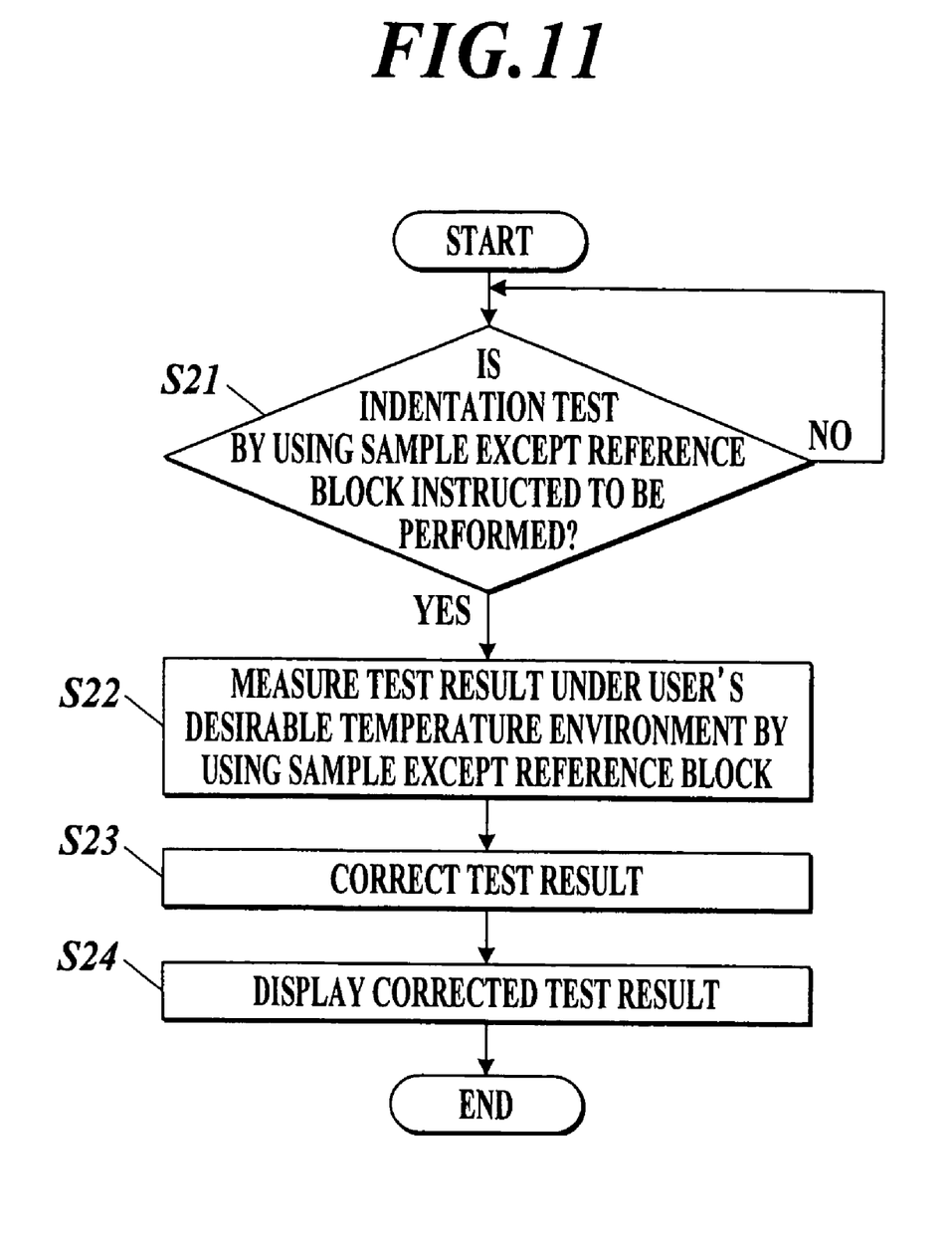
FIG. 11 is a flow chart for explaining an indentation test process by the indentation tester.

A test management method for the indentation tester 100 according to the present invention will be explained with reference to flowcharts of FIGS. 9-11.

<Reference Data Storing Process>

A process of storing the reference data by the indentation tester 100 will be explained with reference to the flowchart of FIG. 9.

First, the CPU 210 judges whether or not it is instructed to store the reference data by user's operation on the operation section 400 (Step S1).

When the CPU 210 judges that it is not instructed to store the reference data in Step 1 (Step S1; No), the CPU 210 repeats the process of Step S1.

On the other hand, when the CPU 210 judges that it is instructed to store the reference data in Step 1 (Step S1; Yes,) the CPU 210 executes the reference block measurement program 232 to measure the reference block as the sample S under a plurality of the temperature environments to obtain the test result (Step 2 (reference block measuring step)). In other words, the CPU 210 measures the curves of the test force vs. the indentation depth under a plurality of the temperature environments by using the reference block as the sample S.

Next, the CPU 210 executes the calculation program 233 to calculate the test error (namely the test error caused by the heat expansion of the whole indentation tester 100 depending on the temperature of the sample S (reference block)) caused by temperature environment based on the obtained test result (Step S3 (calculating step)), so as to generate the data indicating the degree of the heat expansion of the whole indentation tester 100 (Step 4). The CPU 210 then allows the display section 300 to display the generated data (Step S5), allows the reference data storage file 231 to store the generated data, and then ends the process.

<Maintenance Process>

A maintenance process by the indentation tester 100 will be explained with reference to the flowchart of FIG. 10.

First, the CPU 210 judges whether or not it is instructed to perform a maintenance of the indentation tester 100 by user's operation on the operation section 400 (Step S11).

When the CPU 210 judges that it is not instructed to perform the maintenance of the indentation tester 100 in Step S11 (Step 11; No), the CPU 210 repeats the process of Step 11.

On the other hand, when the CPU 210 judges that it is instructed to perform the maintenance of the indentation tester 100 in Step S11 (Step 11; Yes), the CPU 210 executes the reference block measurement program 232 to measure the reference block as the sample S under a plurality of the temperature environments to obtain the test result (Step S12 (reference block measuring step)). In other words, the CPU 210 measures the curves of the test force vs. the indentation depth under a plurality of the temperature environments by using the reference block as the sample S.

Next, the CPU 210 executes the calculation program 233 to measure the test error (namely the test error caused by the heat expansion of the whole indentation tester 100 depending on the temperature of the sample S (reference block)) caused by temperature environment based on the obtained test result (Step S13 (calculating step)), so as to generate the data indicating the degree of the heat expansion of the whole indentation tester 100 (Step S14).

Next, the CPU 210 executes the judgment program 234 to compare the generated data indicating the degree of the heat expansion of the whole indentation tester 100 with the reference data (the data indicating the degree of the heat expansion of the whole indentation tester 1) previously stored in the reference data storage file 231 so as to judge whether or not the test error caused by temperature environment is within a predetermined range (Step S15 (judging step)). The CPU 210 allows the display section 300 to display the judgment result (Step S16), and then ends the process.

<Indentation Testing Process>

A process with respect to the indentation test by the indentation tester 100 will be explained with reference to the flowchart of FIG. 11.

First, the CPU 210 judges whether or not it is instructed to perform the indentation test by using the sample S except the reference block by user's operation on the operation section 400.

When the CPU 210 judges that it is not instructed to perform the indentation test by using the sample S except the reference block (Step S21; NO), the CPU 210 repeats the process of Step 21.

On the other hand, when the CPU 210 judges that it is instructed to perform the indentation test by using the sample S except the reference block (Step S21; Yes), the CPU 210 executes the measurement program 235 to measure the sample S except the reference block under user's desirable temperature environment to obtain the test result (Step S22). In other words, the CPU 210 measures the curves of the test force vs. the indentation depth under user's desirable temperature environment by using the sample S except the reference block.

Next, the CPU 210 executes the correction program 236 to correct the obtained test result based on the reference data (the data indicating the degree of the heat expansion of the whole indentation tester 100) previously stored in the reference data storage file 231 (Step S23 (correcting step)). The CPU 210 allows the display section 300 to display the corrected test result, and then ends the process.

According to the above-mentioned test management method for the indentation tester 100 and the indentation tester 100 of the present invention, a predetermined reference block as the sample S is measured under a plurality of the temperature environments to obtain the test result, and the test error (test error caused by the heat expansion of the whole indentation tester 100 depending on the temperature of the sample S (reference block)) caused by temperature environment is calculated based on the test result to judge whether or not the test error is within a predetermined range.

Therefore, since it is possible to examine whether or not the test error caused by temperature environment is within a predetermined range by using the reference block, a reliability of a measured value of the high-temperature sample S or the low-temperature sample S by the indentation tester 100 can be secured Moreover, according to the test management method for the indentation tester 100 and the indentation tester 100 of the present invention, a predetermined reference block as the sample S is measured under a plurality of the temperature environments to obtain the test result, and the test error (the test error caused by the heat expansion of the whole indentation tester 100 depending on the temperature of the sample S (reference block)) caused by temperature environment is calculated based on the test result to correct the test result of the sample S except the reference block based on the test error.

Therefore, since the test result of the sample S except the reference block can be corrected in view of the test error caused by temperature environment, a reliability of a measured value of the high-temperature sample S or the low-temperature sample S by the indentation tester 100 can be secured Moreover, according to the test management method for the indentation tester 100 and the indentation tester 100 of the present invention, the reference block is composed of any one of fused quartz, single crystal quartz, ceramics, single crystal alumina, and low thermal expansion alloy.

Therefore, since the degree of the heat expansion of the reference block is vanishingly small in comparison with that of the whole indentation tester 100, the test error (the test error caused by the heat expansion of the whole indentation tester 100 depending on the sample temperature) caused by temperature environment can be measured precisely.

Moreover, according to the test management method for the indentation tester 100 and the indentation tester 100 of the present invention, the indentation tester 100 is an instrumented indentation tester to which the heating/cooling mechanism to heat/cool the sample S is attached.

For example, the instrumented indentation tester measures the indentation depth by the indenter 4 in the sample S. Since the indentation depth depends on origin detection accuracy of a tip shape of the indenter 4 or the curve of the test force vs. the indentation depth, or depends on an influence of stiffness of the testing device, it is difficult to make a correction individually for the indentation depth. By examining whether or not the test result caused by temperature environment is within a predetermined range by using the reference block, or by correcting the test result of the sample S in view of the test error caused by temperature environment, it is possible to secure a reliability of a measurement value of the high-temperature sample S or the low-temperature sample S measured by the indentation tester 100 (the instrumented indentation tester) measuring the indentation depth, and it is advantageous.

Incidentally, the present invention is not limited to the embodiments described above, and can be suitably changed without departing from the scope thereof.

The indentation tester 100 may be a Rockwell hardness tester to which a heating/cooling mechanism heating/cooling the sample S is attached.

The Rockwell hardness tester measures the indentation depth by the indenter 4 in the sample S. Since the indentation depth greatly depends on the tip shape of the indenter 4, the reference block valuated by a reference testing device or a reference indenter is a basis for traceability of a measurement value. Therefore, by examining whether or not the test error caused by temperature environment is within a predetermined range by using the reference block, or by correcting the test result of the sample S in view of the test error caused by temperature environment, it is possible to secure a reliability of a measurement value of the high-temperature sample S or the low-temperature sample S by the Rockwell hardness tester, and it is advantageous.

Though it is judged whether or not the test error is within a predetermined range by the hardness testing device, a user also can judge whether or not the test error is within a predetermined range.

In this case, a user may judge whether or not the test error is within a predetermined range by comparing the reference data (the data indicating the degree of the heat expansion of the whole indentation tester 100) previously stored in the reference data storage file 231 which is displayed on the display section 300 with the data indicating the degree of the heat expansion of the whole indentation tester 100 generated when the operation signal for instructing to perform maintenance of the indentation tester is input from the operation section 400, for example.

According to a first aspect of the preferred embodiments of the present invention, a test management method for an indentation tester which includes a control section and forms an indentation on a surface of a heated or cooled sample by pressing an indenter to which a load is applied onto the surface of the sample includes the steps of: measuring a predetermined reference block as the sample under a plurality of temperature environments to obtain a test result; calculating a test error caused by temperature environment based on the test result by the control section; and judging whether or not the test error is within a predetermined range by the control section.

According to a second aspect of the preferred embodiments of the present invention, a test management method for an indentation tester which includes a control section and forms an indentation on a surface of a heated or cooled sample by pressing an indenter to which a load is applied onto the surface of the sample includes the steps of: measuring a predetermined reference block as the sample under a plurality of temperature environments to obtain a test result; calculating a test error caused by temperature environment based on the test result by the control section; and correcting the test result of the sample except the reference block based on the test error by the control section.

Preferably, in the test management method, the reference block is composed of any one of fused quartz, single crystal quartz, ceramics, single crystal alumina, and low thermal expansion alloy.

Preferably, in the test management method, the indentation tester is an instrumented indentation tester or a Rockwell hardness tester to which a heating/cooling mechanism to heat/cool the sample is attached.

According to a third aspect of the preferred embodiments of the present invention, an indentation tester to form an indentation on a surface of a heated or cooled sample by pressing an indenter to which a load is applied onto the surface of the sample includes: a reference block measurement member to measure a predetermined reference block as the sample under a plurality of temperature environments to obtain a test result; a calculation member to calculate a test error caused by a heat expansion of the whole indentation tester depending on a sample temperature based on the test result; and a judgment member to judge whether or not the test error is within a predetermined range.

According to a fourth aspect of the preferred embodiments of the present invention, an indentation tester to form an indentation on a surface of a heated or cooled sample by pressing an indenter to which a load is applied onto the surface of the sample includes: a reference block measurement member to measure a predetermined reference block as the sample under a plurality of temperature environments to obtain a test result; a calculation member to calculate a test error caused by a heat expansion of the whole indentation tester depending on a sample temperature based on the test result; and a correction member to correct the test result of the sample except the reference block based on the test error.

Preferably, in the indentation tester, the reference block is composed of any one of fused quartz, single crystal quartz, ceramics, single crystal alumina, and low thermal expansion alloy.

Preferably, in the indentation tester, the indentation tester is an instrumented indentation tester or a Rockwell hardness tester to which a heating/cooling mechanism to heat/cool the sample is attached.

According to the present invention, a predetermined reference block as the sample is measured under a plurality of the temperature environments to obtain the test result, and the test error (the test error caused by the heat expansion of the whole indentation tester depending on the sample temperature) caused by temperature environment is calculated to judge whether or not the test error is within a predetermined range.

Therefore, since it is possible to examine whether or not the test error caused by temperature environment is within a predetermined range by using the reference block, a reliability of a measurement value of high-temperature sample or low-temperature sample by the indentation tester can be secured.

Moreover, a predetermined reference block as the sample is measured under a plurality of the temperature environments to obtain the test result, and the test error (the test error caused by the heat environment of the whole indentation tester depending on the sample temperature) caused by temperature environment is calculated based on the test result to correct the test result of the sample except the reference block.

Therefore, since it is possible to correct the test result of the sample in view of the test error caused by the teat environment, a reliability of a measurement value of the high-temperature sample or the low-temperature sample by the indentation tester can be secured.

Moreover, as well as obtaining the above advantage, the reference block is composed of any one of fused quartz, single crystal quartz, ceramics, single crystal alumina, and low thermal expansion alloy.

Therefore, since the degree of the heat expansion of the reference block is vanishingly small in comparison with that of the whole indentation tester 100, the test error (the test error caused by the heat expansion of the whole indentation tester depending on the sample temperature) caused by temperature environment can be measured precisely.

Moreover, as well as obtaining the above advantage, the indentation tester is the instrumented indentation tester or the Rockwell hardness tester to which the heating/cooling mechanism heating/cooling the sample is attached.

Therefore, by examining whether or not the test error caused by temperature environment is within a predetermined range by using the reference block, or by correcting the test result of the sample in view of the test error caused by temperature environment, it is possible to secure a reliability of a measurement value of the high-temperature sample or the low-temperature sample measured by the indentation tester (the instrumented indentation tester or the Rockwell hardness tester) measuring the indentation depth, and it is advantageous.

The entire disclosure of Japanese Patent Application No. 2007-210818 filed on Aug. 13, 2007, including specification, claims, drawings and abstract are incorporated herein by reference in its entirety.

Although various exemplary embodiments have been shown and described, the invention is not limited to the embodiments shown. Therefore, the scope of the invention is intended to be limited solely by the scope of the claims that follow.

What is claimed is:

1. A test management method for an indentation tester which includes a control section and forms an indentation on a surface of a heated or cooled sample by pressing an indenter to which a load is applied onto the surface of the sample comprising the steps of:

performing a plurality of measurements on a reference block with known properties of thermal expansion as the sample under a plurality of constant temperature environments each measurement comprising continuously increasing the load to a predetermined maximum test force and continuously decreasing thereafter under each of the constant temperature environments to obtain a test result;

calculating a test error caused by temperature environment based on the test result by the control section; and judging whether or not the test error is within a predetermined range by the control section.

2. The test management method for the indentation tester according to claim 1, wherein the reference block is composed of any one of fused quartz, single crystal quartz, ceramics, single crystal alumina, and low thermal expansion alloy.

3. The test management method for the indentation tester according to claim 1, wherein the indentation tester is an instrumented indentation tester or a Rockwell hardness tester to which a heating/cooling mechanism to heat/cool the sample is attached.

4. A test management method for an indentation tester which includes a control section and forms an indentation on a surface of a heated or cooled sample by pressing an indenter to which a load is applied onto the surface of the sample comprising the steps of:

performing a plurality of measurements on a reference block with known properties of thermal expansion as a first sample under a plurality of constant temperature environments each measurement comprising continuously increasing the load to a predetermined maximum test force and continuously decreasing thereafter under each of the constant temperature environments to obtain a test result;

calculating a test error caused by temperature environment based on the test result by the control section; and using the test result of the first sample to correct the test results of a second sample.

* * * * *